(12) United States Patent
Storm et al.

(10) Patent No.: US 6,756,057 B2
(45) Date of Patent: Jun. 29, 2004

(54) AMOXICILLIN AND POTASSIUM CLAVULANATE DOSAGE FORM

(75) Inventors: Kevin H. Storm, Bristol, TN (US); Creighton P. Conley, Bristol, TN (US); John A. Roush, Kingsport, TN (US)

(73) Assignee: Beecham Pharmaceuticals (pte) Limited, Jurong (SG)

( * ) Notice: Subject to any disclaimer, the term of this patent is extended or adjusted under 35 U.S.C. 154(b) by 0 days.

(21) Appl. No.: 10/462,066

(22) Filed: Jun. 13, 2003

(65) Prior Publication Data

US 2003/0224049 A1 Dec. 4, 2003

Related U.S. Application Data

(63) Continuation of application No. 09/974,572, filed on Oct. 10, 2001, now abandoned.
(60) Provisional application No. 60/239,779, filed on Oct. 12, 2000.

(51) Int. Cl.[7] ................................................. A61K 9/24
(52) U.S. Cl. ...................................... 424/472; 424/468
(58) Field of Search ................................. 424/464, 468, 424/472, 470

(56) References Cited

U.S. PATENT DOCUMENTS

| | | |
|---|---|---|
| 4,110,165 A | 8/1978 | Cole et al. |
| 4,282,202 A | 8/1981 | Dowrick |
| 4,301,149 A | 11/1981 | Crowley |
| 4,441,609 A | 4/1984 | Crowley |
| 4,525,352 A | 6/1985 | Cole et al. |
| 4,537,887 A | 8/1985 | Rooke et al. |
| 4,673,637 A | 6/1987 | Hyman |
| 4,950,484 A | 8/1990 | Olthoff et al. |
| 5,007,790 A | 4/1991 | Shell |
| 5,051,262 A | 9/1991 | Panoz et al. |
| 5,133,974 A | 7/1992 | Paradissis et al. |
| 5,158,779 A | 10/1992 | Gergely et al. |
| 5,225,197 A | 7/1993 | Bolt et al. |
| 5,407,686 A | 4/1995 | Patel et al. |
| 5,445,829 A | 8/1995 | Paradissis et al. |

(List continued on next page.)

FOREIGN PATENT DOCUMENTS

| | | |
|---|---|---|
| EP | 0080862 A1 | 6/1983 |
| EP | 0131147 B1 | 1/1985 |
| EP | 0080862 B1 | 9/1985 |
| EP | 0222914 A1 | 5/1987 |
| EP | 0234670 A2 | 9/1987 |
| EP | 0389177 A | 9/1988 |
| EP | 0396335 A1 | 11/1990 |
| EP | 0131147 B2 | 12/1996 |
| EP | 0281200 A | 12/1996 |
| EP | 1044680 A | 10/2000 |
| GB | 1508977 | 4/1978 |
| GB | 2005538 A | 4/1979 |
| HU | 205 611 B | 4/1991 |
| WO | WO 91/15197 A1 | 10/1991 |
| WO | WO 92/19227 A2 | 11/1992 |

(List continued on next page.)

OTHER PUBLICATIONS

1996 MIMS Annual, "Augmentin," Twentieth Edition, May 1995, pp. 8–476 to 8–477.

(List continued on next page.)

Primary Examiner—Thurman K. Page
Assistant Examiner—Micah Young
(74) Attorney, Agent, or Firm—Dara L. Dinner; Stephen Venetianer; Charles M. Kinzig

(57) ABSTRACT

Bacterial infections may be treated using a high dosage regimen of amoxicillin and potassium clavulanate. Preferably, the dosage is provided by a bilayer tablet.

80 Claims, 1 Drawing Sheet

U.S. PATENT DOCUMENTS

| | | | |
|---|---|---|---|
| 5,487,901 A | 1/1996 | Conte et al. | |
| 5,500,227 A | 3/1996 | Oshlack et al. | |
| 5,582,837 A | 12/1996 | Shell | |
| 5,650,169 A | 7/1997 | Conte et al. | |
| 5,670,170 A * | 9/1997 | Grimmett et al. | 424/489 |
| 5,681,583 A | 10/1997 | Conte et al. | |
| 5,690,959 A | 11/1997 | Palepu et al. | |
| 5,733,577 A | 3/1998 | Myers et al. | |
| 5,738,874 A | 4/1998 | Conte et al. | |
| 5,741,524 A | 4/1998 | Stanisforth et al. | |
| 5,814,337 A | 9/1998 | Merrifield et al. | |
| 5,849,330 A | 12/1998 | Marvola et al. | |
| 5,851,550 A | 12/1998 | Martin et al. | |
| 5,858,412 A | 1/1999 | Stanisforth et al. | |
| 5,861,172 A | 1/1999 | Martin et al. | |
| 5,910,322 A | 6/1999 | Rivett et al. | |
| 5,962,022 A | 10/1999 | Bolt et al. | |
| 5,972,389 A | 10/1999 | Shell et al. | |
| 6,051,254 A | 4/2000 | Merrifield et al. | |
| 6,051,255 A | 4/2000 | Conley et al. | |
| 6,077,536 A | 6/2000 | Merrifield et al. | |
| 6,110,497 A | 8/2000 | Martin et al. | |
| 6,126,969 A | 10/2000 | Shah et al. | |
| 6,136,345 A | 10/2000 | Grimmett et al. | |
| 6,177,421 B1 | 1/2001 | Moir et al. | |
| 6,183,778 B1 | 2/2001 | Conte et al. | |
| 6,183,780 B1 | 2/2001 | Van Balken et al. | |
| 6,214,359 B1 | 4/2001 | Bax | |
| 6,294,199 B1 | 9/2001 | Conley et al. | |
| 6,294,200 B1 | 9/2001 | Conte et al. | |
| 6,299,903 B1 | 10/2001 | Rivett et al. | |
| 6,340,475 B2 | 1/2002 | Shell et al. | |
| 6,352,720 B1 | 3/2002 | Martin et al. | |
| 6,358,528 B1 | 3/2002 | Grimmett et al. | |
| 6,372,255 B1 | 4/2002 | Saslawski et al. | |
| 6,399,086 B1 | 6/2002 | Katzhendler et al. | |
| 2001/0018070 A1 | 8/2001 | Shell et al. | |
| 2001/0026809 A1 | 10/2001 | Oshlack et al. | |
| 2001/0038838 A1 | 11/2001 | Burch | |
| 2001/0043926 A1 | 11/2001 | Burch | |
| 2001/0046984 A1 | 11/2001 | Rudnic | |
| 2001/0048944 A1 | 12/2001 | Rudnic et al. | |
| 2002/0001616 A1 | 1/2002 | Conley et al. | |
| 2002/0004071 A1 | 1/2002 | Cherukuri | |
| 2002/0004499 A1 | 1/2002 | Rudnic et al. | |
| 2002/0006433 A1 | 1/2002 | Davidson et al. | |
| 2002/0064562 A1 | 5/2002 | Martin et al. | |
| 2002/0086056 A1 | 7/2002 | Grimmett et al. | |
| 2002/0099044 A1 | 7/2002 | Bax et al. | |

FOREIGN PATENT DOCUMENTS

| | | | |
|---|---|---|---|
| WO | WO 93/00898 A1 | 1/1993 | |
| WO | WO 94/06416 | 3/1994 | |
| WO | WO 94/16696 | 8/1994 | |
| WO | WO 94/27557 | 12/1994 | |
| WO | WO 94/27600 A1 | 12/1994 | |
| WO | WO 95/20946 | 8/1995 | |
| WO | WO 95/25516 A1 | 9/1995 | |
| WO | WO 95/28148 | 10/1995 | |
| WO | WO 95/28927 * | 11/1995 | A61K/31/43 |
| WO | WO 95/33487 A1 | 12/1995 | |
| WO | WO 96/04907 A1 | 2/1996 | |
| WO | WO 96/04908 | 2/1996 | |
| WO | WO 96/07408 | 3/1996 | |
| WO | WO 96/34605 A1 | 11/1996 | |
| WO | WO 97/09042 | 3/1997 | |
| WO | WO 98/05305 | 2/1998 | |
| WO | WO 98/07424 A1 | 2/1998 | |
| WO | WO 98/22091 * | 5/1998 | A61K/9/10 |
| WO | WO 98/35672 | 8/1998 | |
| WO | WO 98/40054 A1 | 9/1998 | |
| WO | WO 98/42311 A1 | 10/1998 | |
| WO | WO 99/25343 | 5/1999 | |
| WO | WO 99/47125 | 9/1999 | |
| WO | WO 99/62910 | 12/1999 | |
| WO | WO 00/03695 A1 | 1/2000 | |
| WO | WO 00/12088 A1 | 3/2000 | |
| WO | WO 00/23045 | 4/2000 | |
| WO | WO 00/41478 | 7/2000 | |
| WO | WO 00/44353 | 8/2000 | |
| WO | WO 00/6116 | 10/2000 | |
| WO | WO 01/00177 A1 | 1/2001 | |
| WO | WO 01/13883 | 3/2001 | |
| WO | WO 01/56544 A2 | 8/2001 | |
| WO | WO 01/62231 A1 | 8/2001 | |
| WO | WO 01/80824 A2 | 11/2001 | |
| WO | WO 02/30392 | 4/2002 | |
| WO | WO 02/49618 | 6/2002 | |

OTHER PUBLICATIONS

Amendola et al., "Pediatric suspension of amoxycillin and clavulanic acid in the treatment of bacterial infections of the upper respiratory tract and ear", Minerva Pediatrica, Feb. 1989, 41(2), pp. 97–103 (English abstract).

Appelbaum, 1996, "Epidemiology and in vitro susceptibility of drug–resistant Streptococcus pneumoniae," Ped. Inf. Dis. J., 15(10): 932–939.

Arancibia et al., 1987, "Pharmacokinetics and bioavailibility of a controlled release amoxicillin formulation," Int. J. of Clin. Pharm., Ther. and Tox., 25(2): 97–100.

Arguedas et al., "In–vitro activity of cefprozil (BMY 28100) and loracarbef (LY 163892) against pathogens obtained from middle ear fluid", J. Antimicrob. Chemother., 1991, 27, pp. 311–318.

Astruc, "Effectiveness and Safety of a New Formulation Containing 100 mg amoxicillin—12.5 mg clavulanic acid in infants with acute otitis media", Annales De Pediatrie, Feb. 1992, vol. 39, No. 2, 142–148 (with translation).

Aulton et al., "The Mechanical Properties of Hydroxypropylmethylcellulose Films Derived from Aqueous Systems", Drug Development and Industrial Pharmacy, 1981, 7(6), pp. 649–668.

Ball et al., "Clavulanic Acid and Amoxicillin: A Clinical, Bacteriological, and Pharmacological Study", The Lancet, Mar. 22, 1980, pp. 620–623.

Baron et al., "Antimicrobial therapy in acute otitis media", Traitement Antibiotique de L'Otite Moyenne Aiguë, Ann Pédiatr, 1991, 38(8), pp. 549–555 (with translation of abstract).

Barry et al., "Effect of Increased Dosages of Amoxycillin in Treatment of Experimental Middle Ear Otitis Due to Penicillin–Resistant Streptococcus pneumoniae", Antimicrobial Agents and Chemotherapy, Aug. 1993, Vol 37, No. 8, pp. 1599–1603.

Beghi et al., "Efficacy and Tolerability of Azithromycin versus Amoxicillin/Clavulanic Acid in Acute Purulent Exacerbation of Chronic Bronchitis", Journal of Chemotherapy, 1995, 7(2), pp. 146–152.

Behre et al., "Efficacy of Twice–Daily Dosing of Amoxycillin/Clavulanate in Acute Otitis Media in Children", Infection, 1997, 25(3), pp. 163–166.

Berry et al., "Bactericidal and Morphological Effects of Amoxicillin on Helicobacter pylori", Antimicrobial Agents and Chemotherapy, Aug. 1995, vol 39(8), pp. 1859–1861.

Berry et al., "Bacteriological Efficacies of Three Macrolides Compared with Those of Amoxicillin–Clavulanate against *Streptococcus pneumoniae* and *Haemophilus influenzae*", Antimicrobial Agents and Chemotherapy, 1998, vol. 42(12), pp. 3193–3199.

Berry et al., "Comparative efficacy of gemifloxacin in experimental models of pyelonephritis and wound infection", J. Antimicrob. Chemother., Dec. 2000, no 45, supplement S1 pp. 87–93.

Berry et al., Comparative in vivo activity of gemifloxacin in a rat model of respiratory tract infection, J. Antimicrob. Chemother., vol 45, supplement S1, pp. 79–85.

Bottenfield et al., "Safety and tolerability of a new formulation (90 mg/kg/day divided every 12 h) of amoxicillin/clavulanate (Augmentin®) in the empiric treatment of pediatric acute otitis media caused by drug-resistant *Streptococcus pneumoniae*," Pediatr Infect. Dis. J., 1998, vol. 17(10), pp. 963–968.

Brooks et al., "Pleuromutilins, Part 1: The Identification of Novel Mutilin 14–Carbamates", Bioorganic and Medicinal Chemistry 9, 2001, pp. 1221–1231.

Bronner et al., "Ex vivo pharmacodynamics of 1.1 g IV amoxicillin–clavulanic acid against β–lactamase positive *E. coli* in a Yucatan micropig model that mimics human pharmacokinetics (2.2 g IV)", Antibiotiques, 2001, 3: 91–98 (Translation Included).

Burgess et al., "Uptake of clavulanic acid across rat jejunal segments in vitro", J. Physiology, vol 482, p. 41P.

Caillon et al., May 1998, "Dynamics of the bacteriacidae activity of ofloxacin–amoxicillin and ofloxacin–clavulanic acid against pathogen bacteria of the respiratory tract", Pathologie Biologie, 36(5), pp. 414–419.

Calver et al., "Amoxicllin/Clavulanate (A/C) BID vs A/C TID in the Treatment of Lower Respiratory Tract Infections (LRTI)", Abstracts of the 35th ICAAC, 1995, p. 334.

Calver et al., "Augmentin BID Versus Augmentin TID in the Treatment of Lower Respiratory Tract Infections", Can. J. Infect Dis., Jul. 1995, Vol 6 Suppl C, Abstract No. 0338, p. 239C Abstract.

Calver et al., "Dosing of Amoxicillin/Clavulanate Given Every 12 Hours is as Effective as Dosing Every 8 Hours for Treatment of Lower Respiratory Tract Infection", Clinical Infectious Disease, Apr. 1997, 24, pp. 570–574.

Caron et al., "Effects of Amoxicllin–Clavulanate Combination on the Motility of the Small Intestine in Human Beings", Antimicrobial Agents and Chemotherapy, Jun. 1991, vol. 35, No. 6, pp. 1085–1088.

Cars, "Efficacy of Beta–lactam Antibiotics: Integration of Pharmacokinetics and Pharmacodynamics", Diagn Microbiol Infect Dis, 1997, 27 pp. 29–33.

Catherall et al., "Distribution and Efficacy Studies with Ticarcillin–Clavulanic Acid (Timentin) in Experimental Klebsiella Pneumoniae Meningitis in Rabbits", Journal of Chemotherapy, 1989 supplement no 4, pp. 80–81.

Chan et al., "A Comparative Study of Amoxicllin–Clavulanate and Amoxicllin. Treatment of Otitis Media with Effusion," Archives of Otolaryngology—Head and Neck Surgery, Feb. 1988, pp. 142–146.

Chiou, "Critical Evaluation of the Potential Error in Pharmacokinetic Studies of Using the Linear Trapezoidal Rule Method for the Calculation of the Area Under the Plasma Level–Time Curve," 1978, J. Pharmicokinet. Biopharm., 6(6): 539–546.

Connor et al., "High Resolution $^1$H NMR Spectroscopic Studies of the Metabolism and Excretion of Amplicillin in Rats and Amoxycillin in Rats and Man", Journal Pharm. Pharmacol. 1994, vol 46 pp. 128–134.

Cook et al., "Efficacy of Twice–Daily Amoxycillin/Clavulanate ('Augmentin–Duo' 400/57) in Mild to Moderate Lower Respiratory Tract Infection in Children", BJCP, 50(3), Apr./May 1996, pp. 125–128.

Cooper et al., "Effect of low concentrations of clavulanic acid on the in–vitro activity of amoxycillin against β–lactamase–producing *Branhamella catarrhalis* and *Haemophilus influenzae*", Journal of Antimicrobial Chemotherapy, 1990, vol. 26, pp. 371–380.

Craig et al., "Killing and Regrowth of Bacteria in Vitro: A Review", Scand J Infect Dis., 1991, Suppl 74, pp. 63–70.

Craig, "Antimicrobial Resistant Issues of the Future", Diagn Microbiol Infect Dis, 1996, 25, pp. 213–217.

Craig, "Pharmacokinetic/Pharmacodynamic Parameters: Rationale for Antibacterial Dosing of Mice and Men", Clinical Infectious Diseases, Jan. 1998, 26, pp. 1–12.

Craig et al., "Pharmacokinetics and pharmacodynamics of antibiotics in otitis media", Pediatr Infect Dis J, 1996, 15(10), pp. 944–948 (Reprint).

Crokaert et al., "Activities of Amoxicllin and Clavulanic Acid Combinations Against Urinary Tract Infections", Antimicrobial Agents and Chemotherapy, Aug. 1982, Vol 22 No. 2, pp. 346–349.

Dagan et al., "Bacteriologic and clinical efficacy of high dose amoxicillin/clavulanate in children with acute otitis media", Pediatric Infectious Diseases Journal, Sep. 2001, vol 20(9), pp. 829–837.

Dagan et al., Bacteriological and Clinical Efficacy of a New Amoxicllin/Clavulanate Extra Strength formulation in the Treatment of Acute Otitis Media (AOM), Abstract 107 from the 40$^{th}$ ICAAC, Sep. 17–20, 2000, p. 491.

Ellis–Pegler et al., "Augmentin treatment of bacterial infections in hospitalized patients", New Zealand Medical Journal, 1982, 95, pp. 542–545.

Everett et al., "$^{19}$F NMR Spectroscopy Study of the Metabolites of Flucloxacillin in Rat Urine," Journal of Pharm. Pharmacology, 1985, vol 37, pp. 869–873.

Everett et al., "A Study of Flucloxacillin Metabolites in Rat Urine by Two–Dimensional $^1$F COSY NMR," Journal of Pharmaceutical & Biomedical Analysis, 1989, vol 7, no 3, pp. 397–403.

Everett et al., "Spin–echo $^1$H N.M.R. spectroscopy: A new method for studying penicillin metabolism," J. Chem. Soc. Chem. Commun., 1984, pp. 894–895.

Feldman et al., "Twice–daily antibiotics in the treatment of acute otitis media: trimethoprim–sulfamethoxazole versus amoxicillin–clavulanate", Can Med. Assoc. J., 1990, 142(2): 115–118.

Finch, "Pneumonia: The Impact of Antibiotic Resistance on its Management", Microbial Drug Resistance, Vol 1, No. 2, 1995, pp. 149–158.

Fink et al., "A trial of orally administered Augmentin in the treatment of urinary tract infection and lower respiratory tract infection in a children's hospital", Proc Eur Symp on Augmentin, Scheveningen Jun. 1982, 1983: pp. 325–333.

Flatulence, Diarrhoea, and Polyol Sweetners, The Lancet, Dec. 3, 1983, vol. II, p. 1321.

Fraschini et al., "Pharmacokinetics and Tissue Distribution of Amoxicillin plus Clavulanic Acid after Oral Administration in Man", Journal of Chemotherapy, 1990, 2(3), pp. 171–177.

Friedland et al., "Management of Infections caused by Antibiotic–Resistant *Streptococcus pneumoniae*", The New England Journal of Medicine, Aug. 1994, vol. 331, No. 6, pp. 377–382.

Geneva Pharmaceuticals, Inc., et al. v. GlaxoSmithKline PLC, et al.: The Opinion and Order rendered on Jul. 19, 2002 (as issued by the court).

Geneva Pharmaceuticals, Inc., et al. v. GlaxoSmithKline PLC, et al.: The Opinion and Order rendered on Jul. 19, 2002 (as published by West Law at 2002 WL 1802991).

Geneva Pharmaceuticals, Inc., et al. v. GlaxoSmithKline PLC, et al.: The trial transcript of May 23, 2002 relating to the Court's decision of Jul. 19, 2002.

Geneva Pharmaceuticals, Inc., et al. v. GlaxoSmithKline PLC, et al.: The Opinion and Order rendered Apr. 22, 2002.

Geneva Pharmaceuticals, Inc., et al. v. GlaxoSmithKline PLC, et al.: the trial transcript of Mar. 13, 2002, relating to the Court's decision of Apr. 22, 2002.

Geneva Pharmaceuticals, Inc., et al. v. GlaxoSmithKline PLC, et al.: the Opinion and Order rendered Feb. 25, 2002.

Geneva Pharmaceuticals, Inc., et al. v. GlaxoSmithKline PLC, et al.: the trial transcript of Dec. 14, 2001, relating to the Court's decision of Feb. 25, 2002.

Greenwood, D., "Short Communication: a type of interaction between clavulanic acid and other β–lactam antibiotics distinct from the β–lactamase inhibition effect," from Augmentin: clavulanate–potentiated amoxycillin, Proceeding of the First Symposium, Jul. 3–4, 1980, pp. 80–83.

Handbook of Pharmaceutical Excipients, Third Edition, "Mannitol," 1986, Edited by Arthur H. Kibbe, Ph.D., pp 324–328.

Hannan et al., "In Vitro Activity of Gemifloxacin (SB 265805; LB 20304a) against human mycoplasmas," Journal of Antimicrobial Chemotherapy, 2000, vol 45, pp. 367–369.

Heikkinen et al., "Short–term use of amoxicillin–clavulanate during upper respiratory tract infection for prevention of acute otitis media", The Journal of Pediatrics, Feb. 1995, 126(2), pp. 313–316.

Hilton et al., 1992, "In vitro and in vivo evaluation of an oral sustained–release floating dosage form of amoxycillin trihydrate," Intl. J. of Pharmaceutics, 86: 79–88.

Hilton et al., 1993, "Use of Hydroxypropyl Methylcellulose Acetate Succinate in an Enteric Polymer Matrix to Design Controlled–Release Tablets of Amoxicillin Trihydrate", J. Pharmaceutical Sciences, 82(7): 737–743.

Hoberman et al., "Efficacy of amoxicillin/clavulanate for acute otitis media: relation to *Streptococcus pneumoniae* susceptibility", Pediatr Infect Dis J., Oct. 1996, 15(10), pp. 955–962.

Hoberman et al., "Equivalent efficacy and reduced occurrence of diarrhea from a new formulation of amoxycillin/clavulanate potassium (Augmentin®) for treatment of acute otitis media in children", Pediatrc Infect. Dis. J., May 1997, 16(5), pp. 463–470.

Hoffman, et al., 1998, "Pharmacodynamic and Pharmacokinetic rationales for the development of an oral controlled–release amoxicillin dosage form," J. Controlled Release, 54: 29–37.

Hol et al., "Experimental evidence for Moraxella–induced penicillin neutralization in pneumococcal pneumonia", Journal of Infectious Diseases, 1994, 170, pp. 1613–1616.

Jacobsson et al., "Evaluation of Amoxicillin Clavulanate Twice Daily versus Thrice Daily in the Treatment of Otitis Media in Children", Eur. J. Clin. Microbiol. Infect. Dis., May 1993, 12(5): 319–324.

Jeffries et al., "An Initial Assessment of Augmentin for the Treatment of Paediatric Infections in General Practice", The British Journal of Clinical Practice, 1996, pp. 61–66.

Ji et al., "Identification of Critical Staphylococcal Genes Using Conditional Phenotypes Generated by Antisense RNA," Science Reprint, Sep. 21, 2001, vol 293, pp. 2266–2269.

Ji et al., "Regulated Antisense RNA Eliminates Alpha–Toxin Virulence in *Staphylococcus aureus* Infection", Journal of Bacteriology, Nov. 1999, pp. 6585–6590.

Klein, "Antimicrobial Agents", Therapeutics—Part V, from the *Textbook of Pediatric Infectious Diseases, 3rd Edition*, vol. II, Editors R. D. Feigin and J. D. Cherry, 1992, pp. 2179–2198.

Kucer et al., "Ampicillin–like penicillins—Amoxycillin, Epicillin Cyclacillin, Hetacillin, Pivampicillin, Talampicillin, Bacampicillin and Metampicllin", 2) "Clavulanic Acid", The Use of Antibiotics, 1987, pp. 172–195/271–286.

Lachman et al., "Tablet Granulations", The Theory and Practice of Industrial Pharmacy, 1986, pp. 314–320.

Legent et al., "A Double–Bind Comparison of Ciprofloxacin and Amoxicillin/Clavulanic Acid in the Treatment of Chronic Sinusitis", Chemotherapy, 1994 40(Suppl. 1), 8–15.

Lerk et al., "Interactions of lubricants and colloidal silica during mixing with excipients", Pharmacuetica Acta Helvetiae, 1977, 52(3) pp. 33–39.

Lieberman et al., "Pharmaceutical Dosage Forms—Tablets Second Edition, Revised and Expanded", 1990, vol. 2, pp. 317–335.

Lister et al., "Rationale behind High–Dose Amoxycillin Therapy for Acute Otitis Media Due to Penicllin–Nonsuseptible Pneumococci: Support from In Vitro Pharmacodynamic Studies", Antimicrobial Agents and Chemotherapy, Sep. 1997, vol. 41, no 9, pp. 1926–1932.

Mandell et al., "Beta–Lactamase Inhibitors, Antimicrobial Agents (cont.)," Goodman and Gillman's The Pharmacological Basis of Therapeutics, $8^{th}$ edition, The Macmillan Company, 1990, p. 1093.

Martindale, The Extra Pharmacopoeia, Thirtieth Edition, "Amoxycillin" and "Clavulanic Acid," Edited by James E. F. Reynolds, The Pharmaceutical Press, 1993, pp. 115–116 and 148.

McCraken "Emergence of resistant *Streptococccus pneumoniae*: a problem in pediatrics", Pediatr Infect Dis J, May 1995, 14(5), pp. 424–428.

McLaren et al., "A comparison of the efficacy and tolerability of Augmentin 625 mg po bd versus Augmentin 375 mg po tds in the treatment of acute bacterial exacerbations of chronic bronchitis", British Journal Clin Research, 1994, 5 pgs 1–10.

Merck Index, Eleventh Edition, "Amoxycillin" and "Clavulanic Acid," Edited by S. Budavari et al., Merck & Co., Inc., 1989, pp. 612 and 2342–2343.

Mizen et al., "A Critique of Animal Pharmacokinetics", Journal of Antimicrobial Chemotherapy, 1988, vol 21, pp. 273–280.

Mizen et al., "Simulation of Human Serum Pharmacokinetics of Ticarcillin–Clavulanic Acid and Ceftazidime in Rabbits and Efficacy Against Experimental Klebsiella Pneumoniae Meningitis", Antimicrobial Agents and Chemotherapy, May 1989, vol 33, No. 5, pp. 693–699.

Mizen et al., "The Influence of Uptake from the Gastrointestinal Tract and First–pass Effect on Oral Bioavailability of (Z)–alkyloxyimino Penicillins", Journal of Pharm. Pharmacology, 1995, vol 47, pp. 725–730.

Moonsammy et al., "Improved Safety Profile of a New Amoxicillin/Clavulanate (A/C) Adult BID Formulation Compared with the Standard A/C TID Formulation", Abstracts of the 36th ICAAC, Chapter 20, poster LM51, 1996, p. 290.

Neu, "Other β–Lactam Antibiotics", Principles and Practice of Infectious Diseases, 1990, pp. 257–263.

Neville, "Augmentin: An in vitro study of bacterial sensitivities to asynergistic combination", New Zealand Medical Journal, 1982, 95, pp. 579–581.

Nicolau et al., "Antibiotic Kinetics and Dynamics for the Clinician", The Medical Clinics of North America Antimicrobial Therapy I, May 1995, vol. 79(3): 477–495.

Okhamafe et al., "Characterization of moisture interactions in some aqueous–based tablet film coating formulations", Journal Pharm Pharmacol, 1985, 37, pp. 385–390.

Pankuch et al., "Comparative activity of ampicillin, amoxycillin, amoxycillin/clavulanate and cefotaxime against 189 penicillin–susceptible and—resistant pneumococci", Journal of Antimicrobial Chemotherapy, 1995, 35, 883–888.

Parrott, "Densification of Powders by Concavo–Convex Roller Compactor", Journal of Pharm Sciences, Mar. 1981, Vol 70(3), pp. 288–291.

Physicians' Desk Reference, 1998, $52^{nd}$ Edition, Medical Economics Co., Montvale, NJ, p. 2798–2805.

Physicians' Desk Reference, $40^{th}$ Edition, 1986, "Amoxycillin," pp. 1315–1316.

Pichichero, "Resistant respiratory pathongens and extended–specturm antibiotics", American Family Physican, 1995, 52(6), pp. 1739–1746.

Prescribing for Children, British National Formulary, vol. 29, p. 11.

Remington's Pharmaceutical Sciences, Eighteenth Edition, 1990, pp. 1304–1308, 1317–1323.

Repertorio Farmaceutico Italiano, 3rd Edition 1989, A106 to A108. (Translation Included).

Robinson, "Amoxycillin trihydrate/Clavulanic acid potassium salt", Med. Actual. Drugs of Today, 1982, 18(5) pp. 213–219.

Ruberto et al., "Amoxycillin and Clavulanic Acid in the Treatment of Urinary Tract Infections in Children", Journal of International Medical Research, 1989, 17: 168–171.

Saarnivaara et al., "Effect of Storage on the Properties of Acetylsalicylc Acid Tablets Coated with Aqueous Hydroxypropyl Methyl–Cellulose Dispersion", Drug Develop and Ind Pharmacy, 1985, 11(2&3), pp. 481–492.

Sakellariou et al., "An evaluation of the interaction and plasticizing efficiency of the polyethylene glycols in ethyl cellulose and hydroxypropyl methylcellulose films using the torsional braid pendulum", Int Journal of Pharm, 1986, 31, pp. 55–64.

Segatore, et al., 1993, "In vitro Activity of Cefodizime (HR–221) in Combination with β–Lactamase Inhibitors," Journal of Chemotherapy, vol. 5, No. 3, pp. 147–150.

Slocombe et al., "In Vitro and In Vivo Activity of Temocillin", Research and Clinical Forums, vol 12, no 5, pp. 21–31.

Staniforth et al., "Effect of food on the bioavailability and tolerance of clavulanic acid/amoxycillin combination", Journal of Antimicrobial Chemotherapy, 1982, 10, pp. 131–139.

Stein et al., "Amoxicillin–potassium clavulanate, a β–lactamase–resistant antibiotic combination", Clinical Pharmacy, vol. 3, Nov.–Dec. 1984 pp. 591–599.

Sumita et al., 1991, "In vitro Synergistic Activity between Meropenem and other Beta–Lactams against Methicillin–Resistant *Staphylococcus aureus*," European Journal of Clinical Microbiology and Infectious Diseases, vol. 10, No. 2, pp. 77–84.

The Use of Antibiotics, 4th Edition, "Clinical Uses of the Drug –amoxycillin/clavulanic acid," J. B. Lippincott Company, 1987 pp. 278–279.

Therapeutic Drugs, "Clavulanate (potassium)," Dollery, 1999, pp. C253–C256.

Todd et al., "Amoxicillin/Clavulanic Acid—An Update of its Antibacterial Activity, Pharmcokinetic Properties and Therapeutic Use", Drugs, 1990, 39(2), pp. 264–307.

Toh, "Amoxycillin with clavulanic acid", The Autstralian Nurses Journal, Dec./Jan. 1989, vol. 18, No. 6, p. 23, Abstract.

Tondachi et al., "Tablet Coating in an Aqueous System", Drug Develop and Ind Pharmacy, 1977, 3(3), pp. 227–240.

van Niekerk et al., "Pharmacokinetic Study of a Paediatric Formulation of Amoxycillin and Clavulanic Acid in Children", European Journal of Clinical Pharmacology, 1985, 29, pp. 235–239.

Vidal 1994, "Augmentin—oral forms," 70th Edition, pp. 132–134 (Translation included).

Woodnutt et al., "Acetate entry rate into portal and peripheral blood in the rabbit", Proc. Nutr. Soc., 1979, vol 38, p. 72A.

Woodnutt et al., "Acetate Metabolism By Tissues of the Rabbit", Comp. Biochemical Physiol, 1986, vol 85B, no 2, pp. 487–490.

Woodnutt et al., "Effect of Protein Binding on Penetration of β–Lactams into Rabbit Peripheral Lymph"Antimicrobial Agents and Chemotherapy, Dec. 1995, vol 39, no 12, pp. 2678–2683.

Woodnutt et al., "Efficacité de l'association amoxicillie–acide clavulanique dans un modèle d'abcès sous–cutané á E. coli chez le rat après simulation de l'administration chez l'homme de 1 g/200 mg (IVD) ou de 2 g/200 mg (perfusion). La lettre de l'infectiologie de la microbiologie a la clinique". Numero hors–serie. Feb. 1995, pp. 23–26.

Woodnutt et al., "Efficacy of High–Dose Amoxicillin–Clavulanate against Experimental Respiratory Tract Infections Caused by Strains of *Streptococcus pneumoniae*", Antimicrobial Agents and Chemotherapy, Jan. 1999, 43(1), 35–40.

Woodnutt et al., "Evaluation of reduced dosing schedule of amoxicllin (AMX) using two pharmacodynamic modes", Abstracts of the 35th Interscience Conference on Antimicrobial Agents and Chemotherapy, Sep. 17–20, 1995, A40, p. 8.

Woodnutt et al., "Influence of stimulated human pharmacokinetics on the efficacy of temocillin against a Klebsiella Pneumoniae meningitis infection in the rabbit", Journal of Chemotherapy, 1989, supplement No. 4, pp. 475–476.

Woodnutt et al., "Penetration of amoxycillin, ticarcillin and clavulanic acid into lymph after intravenous infusion in rabbits to simulate human serum pharmacokinetics", Journal of Antimicrobial Chemotherapy, 1990, vol 26, pp. 695–704.

Woodnutt et al., "Penetration of augmentin and timentin into lymph after simulation of human serum pharmacokinetics in the rabbit", J. Drug Devel. 1989, 2, Supplement 1, pp. 123–126.

Woodnutt et al., "Pharmacodynamics to Combat Resistance", Journal of Antimicrobial Chemotherapy, 2000, vol 46, Topic T1, pp. 25–31.

Woodnutt et al., "Pharmacokinetics and Distribution of Ticarcillin–Clavulanic Acid (Timentin) in Experimental Animals", Antimicrobial Agents and Chemotherapy, 1987, vol 31, no 11, pp. 1826–1830.

Woodnutt et al., "Rabbit liver acetyl–CoA synthetase", Biochem J., 1978, vol 175, pp. 757–759.

Woodnutt et al., "Simulation of Human Serum Pharmacokinetics of Cefazolin, Piperacillin, and BRL 42715 in Rats and Efficacy Against Experimental Intraperitoneal Infections", Antimicrobial Agents and Chemotherapy, Jul. 1992, vol 36, No. 7, pp. 1427–1431.

Woodnutt et al., "Temocillin Efficacy in Experimental Klebsiella Pneumoniae Meningitis after Infusion into Rabbit Plasma To Simulate Antibiotic Concentrations in Human Serum", Antimicrobial Agents and Chemotherapy, Nov. 1988, vol 32, no 11, pp. 1705–1709.

Woodnutt et al., "Two Pharmacodynamic Models for Assessing the Efficacy of Amoxicillin–Clavulanate against Experimental Respiratory Tract Infections Caused by Strains of *Streptococcus pneumoniae*", Antimicrobial Agents and Chemotherapy, Jan. 1999, vol 43, no 1, pp. 29–34.

* cited by examiner

Figure 1
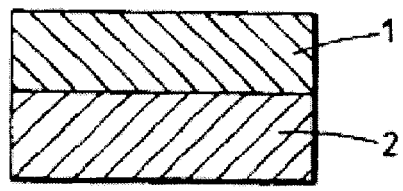
Fig. 1A
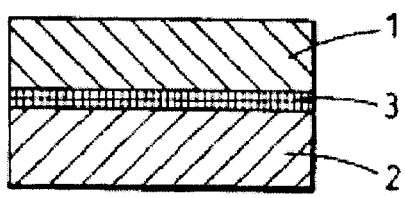
Fig. 1B
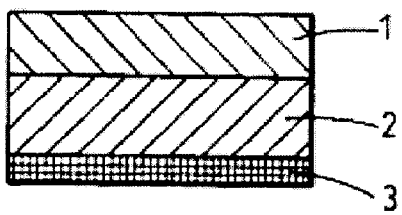
Fig. 1C
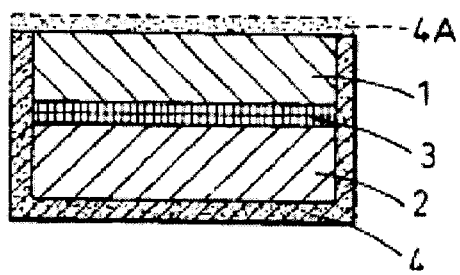
Fig. 1D
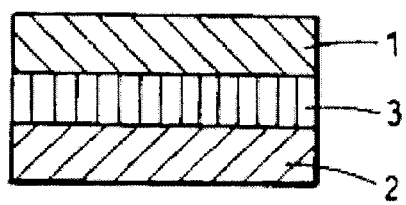
Fig. 1E

AMOXICILLIN AND POTASSIUM CLAVULANATE DOSAGE FORM

This application is a continuation of U.S. Ser. No. 09/974,572 filed Oct. 10, 2001 now abandoned, which claims the benefit of priority from Provisional Application No. 60/239,779 filed Oct. 12, 2000.

This invention relates to a novel formulation comprising using amoxicillin and potassium clavulanate and the use thereof in treating bacterial infections.

Amoxicillin and potassium clavulanate are respectively a known β-lactam antibiotic and a known β-lactamase inhibitor. Products comprising amoxicillin and potassium clavulanate are marketed under the trade name "Augmentin" by SmithKline Beecham. Such products are particularly effective for treatment of community acquired infections, in particular upper respiratory tract infections in adults and otitis media in children.

Various tablet formulations of amoxicillin and potassium clavulanate have been approved for marketing, comprising various different weights and ratios of amoxicillin and potassium clavulanate, for instance, conventional swallow tablets comprising 250/125, 500/125, 500/62.5, and 875/125 mg amoxicillin/clavulanic acid (in the form of potassium clavulanate). Such tablets comprise amoxicillin and clavulanic acid in the ratio 2:1, 4:1, 8:1 and 7:1, respectively. The 875/125 mg tablet was developed to provide a tablet formulation which could be administered in a bid (twice daily) dosage regimen. It is also marketed for tid (three times daily) dosing, in Italy and Spain. The 500/62.5 mg tablet was also developed to provide a tablet formulation which could be administered in a bid dosage regimen, two such tablets being taken every 12 h, in preference to a single 1000/125 mg tablet. A 1000/125 mg single dosage is also available, in France, but as a single dosage sachet rather than a tablet. Typically, the approved regimens provides a single dosage of 125 mg of potassium clavulanate. In addition, WO 97/09042 (SmithKline Beecham) describes tablet formulations comprising amoxicillin and clavulanic acid in a ratio in the range 12:1 to 20:1, preferably 14:1. WO 94/16696 (SmithKline Beecham) discloses generally that clavulanic acid may unexpectedly enhance the efficacy of amoxicillin against microorganisms having a resistant mechanism which is not β-lactamase mediated.

Existing marketed tablet formulations of amoxicillin and potassium clavulanate are conventional in that they provide immediate release of the active ingredients once the tablet reaches the stomach. There has also been some interest in developing formulations in which the release profile is modified, to allow for a longer interval between dosages, for instances, every 12 hours (bid, q12 h), rather than every 8 hours (tid, q8 h).

Thus, for instance, WO 95/20946 (SmithKline Beecham) describes layered tablets comprising amoxicillin and, optionally, potassium clavulanate, having a first layer which is an immediate release layer and a second layer which is a slow release layer. The broadest ratio of amoxicillin to clavulanic acid is 30:1 to 1:1, with a preferred range of 8:1 to 1:1. Amoxicillin is suitably in the form of amoxicillin trihydrate. Examples provided in WO 95/20946 of such bilayered tablets have amoxicillin trihydrate in the immediate release layer and amoxicillin plus clavulanate in the slow release layer. Multi-layered tablets are described more generically in WO 94/06416 (Jagotec AG). Further bilayered tablets comprising clavulanic acid and amoxicillin are described in WO 98/05305 (Quadrant Holdings Ltd). In such tablets, a first layer comprises amoxicillin and a second layer comprises clavulanate and the excipient trehalose, to stabilise the clavulanate component.

In addition, WO 95/28148 (SmithKline Beecham) describes amoxicillin/potassium clavulanate tablet formulations having a core containing amoxicillin and potassium clavulanate coated with a release retarding agent and surrounded by an outer casing layer of amoxicillin and potassium clavulanate. The release retarding agent is an enteric coating, so that there is an immediate release of the contents of the outer core, followed by a second phase from the core which is delayed until the core reaches the intestine. Furthermore, WO 96/04908 (SmithKline Beecham) describes amoxicillin/potassium clavulanate tablet formulations which comprise amoxicillin and potassium clavulanate in a matrix, for immediate release, and granules in a delayed release form comprising amoxicillin and potassium clavulanate. Such granules are coated with an enteric coating, so release is delayed until the granules reach the intestine. WO 96/04908 (SmithKline Beecham) describes amoxicillin/potassium clavulanate delayed or sustained release formulations formed from granules which have a core comprising amoxicillin and potassium clavulanate, surrounded by a layer comprising amoxicillin. WO 94/27557 (SmithKline Beecham) describes controlled release formulations of amoxicillin and clavulanic acid prepared using a hydrophobic waxy material which is then subjected to thermal infusion.

Controlled release formulations comprising amoxicillin have been described by several groups. Thus, Arancibia et al ((Int J of Clin Pharm, Ther and Tox, 1987, 25, 97–100) describe the pharmacokinetic properties and bioavailability of a controlled release formulation comprising 500 mg of amoxicillin. No further details of the formulation are provided. The formulation was however designed to release 21 to 35% during the first 60 minutes, 51 to 66% at 4 hours, 70 to 80% at 6 hours, 81 to 90% at 8 hours and more than 94% at 12 hours. They however found little, if any, correlation between the in vitro dissolution rate and the pharmacokinetic behaviour in the body. Hilton et al (International Journal of Pharmaceutics, 1992, 86, 79–88) described an alternative controlled release tablet having a hydrophilic polymer matrix and a gas release system, to provide intragastric buoyancy, to enhance gastric retention time. This showed no advantage over a conventional capsule formulation, with bioavailability being diminished. In contrast, Hilton et al (Journal of Pharmaceutical Sciences, 1993, 82, 737–743) described a 750 mg controlled release tablet incorporating the enteric polymer hydroxypropylmethyl cellulose acetate succinate. This however failed to show any advantage over a conventional capsule. In particular, the bioavailability was reduced to 64.6% compared with the same dosage provided in a capsule. More recently, Hoffman et al (Journal of Controlled Release, 1998, 54, 29–37 and WO 98/22091) have described a tablet comprising 500 mg of amoxicillin in a matrix comprising hydroxypropyl methyl cellulose, designed to release 50% of its contents in the first three hours and complete the drug release process over eight hours. The time above MIC was found to be significantly extended, compared to a capsule formulation, but not enough for a 12 h dosing interval. The discussion is in the context of a theoretical MIC of 0.2 $\mu$g/ml.

Part of the challenge in providing formulations of amoxicillin in which the drug release is effectively modified (and a ready explanation for the lack of success in the studies already referenced) is the relatively narrow window for absorption of the drug in the small intestine and the relatively short elimination half life of the drug. Furthermore, the rapid elimination of amoxicillin (half-life is about 1.3 hours) makes it difficult to maintain serum levels as clearance from the body is very rapid. Absorption over a prolonged period is therefore required to maintain adequate circulating concentrations of amoxicillin.

In existing tablet formulations comprising amoxicillin and potassium clavulanate, amoxicillin is present in the form amoxicillin trihydrate, as the use of this form provides tablets with greater storage stability than those in which amoxicillin is present as sodium amoxicillin (see GB 2 005 538, Beecham Group Ltd). Sodium amoxicillin is, however, used as the amoxicillin component in existing formulations of amoxicillin and potassium clavulanate adapted for i.v. administration. The form of sodium amoxicillin used is a spray-dried form. In addition, EP 0 131 147-A1 (Beecham Group plc) describes a further form of sodium amoxicillin, so-called "crystalline sodium amoxicillin". A further process for preparing salts of amoxicillin, including sodium amoxicillin, is described in WO 99/62910 (SmithKline Beecham). Sodium amoxicillin is relatively water soluble in comparison to amoxicillin trihydrate.

Formulations comprising clavulanic acid and a pharmaceutically acceptable organic acid or a salt-like derivative thereof, for example calcium citrate, have been described in WO 96/07408 (SmithKline Beecham). In such formulations, it is postulated that the presence of the calcium citrate would help suppress the gastro-intestinal intolerance associated with oral dosing of clavulanate-containing products.

Furthermore, U.S. Pat. No. 5,051,262 (Elan Corp) describes the incorporation of an organic acid into a modified release formulation, to provide a microenvironment in which the locally modified pH helps to protect the active ingredient from degradation.

For β-lactams, including amoxicillin, it is recognised that the time above minimum inhibitory concentration (T>MIC) is the pharmacodynamic parameter most closely related to efficacy. For amoxicillin/clavulanate, killing was observed when serum concentrations exceeded the MIC for only 30% of the dosing interval (Craig and Andes, Ped Inf Dis J, 1996, 15, 255–259).

A further parameter which may be of importance is the ratio of the maximum plasma concentration (Cmax) to the MIC value, as this may be related to the potential to select for resistance. Too low a ratio may encourage the development of resistant strains. Preferably, the plasma $C_{max}$ value is well above the MIC value, for instance, at least two times, more preferably at least three times, most preferably at least four times, the MIC value.

In a clinical study using the existing Augmentin 875/125 mg tablet, it was found that, when dosed at 12 hour intervals, the T>MIC was about 40% for an MIC of 2 μg/ml but only about 30% for an MIC of 4 μg/ml. The existing Augmentin 875/125 mg tablet has a $C_{max}$ value of 11.6±2.8 μg/ml (Physicians Desk Reference, Medical Economics Co, 52 edition, 1998, 2802).

PCT/IB00/00992 describes a new modified release formulation of amoxicillin and clavulanate, comprising for instance, a 1000/62.5 mg bilayer tablet which has an immediate release layer comprising about 563 mg amoxicillin and 62.5 mg clavulanate and a slow release layer comprising about 483 mg of sodium amoxicillin in combination with citric acid and xanthan gum as release modifying excipients. In addition, this application describes a BID dosage regimen using two of these tablets, every 12 hours, for treating bacterial infections, which regimen provides a T>MIC of at least 4.8 h, for an MIC of 4 μg/ml and a T>MIC of about 4.8 h, for an MIC of 8 μg/ml. Such a regimen is particularly useful for treating penicillin resistant S. pneumoniae (PRSP). Penicillin resistance in S. pneumoniae can be assessed according to criteria developed by the National Committee for Clinical Laboratory Standards (NCCLS), as follows: susceptible strains have MICs of <0.06 μg/ml, intermediate resistance is defined as an MIC in the range 0.12 to 1.0 μg/ml whilst penicillin resistance is defined as an MIC of ≧2 μg/ml.

There still however remains an unmet need to provide new formulations of amoxicillin/clavulanate which are effective against a higher target MIC, to provide continuing clinical efficacy against more resistant Drug/Penicillin Resistant S pneumoniae (D/PRSP).

Accordingly, in a first aspect, the present invention provides for a pharmaceutical formulation to provide a unit dosage of amoxicillin and potassium clavulanate which comprises from 100 to 150 mg of potassium clavulanate and from 1700 to 2500 mg of amoxicillin; which formulation is a modified release formulation comprising an immediate and a slow release phase and in which all of the potassium clavulanate and from 0 to 50% of the amoxicillin is in an immediate release phase and from 50 to 100% of the amoxicillin is in a slow release phase; such that the mean T>MIC is at least 4 h for an MIC of 8 μg/ml.

Typically, the unit dosage comprises about 125 mg of potassium clavulanate.

Preferably, the unit dosage comprises from 1900 to 2250, typically about 2000 mg of amoxicillin.

Preferably, the slow release phase comprises from 60 to 90, more preferably 70 to 90, yet more preferably 76 to 90% of the total amoxicillin content.

Preferably, the mean T>MIC is at least 4.2, 4.4, 4.6, 4.8 h.

Representative unit dosages include 1750/125, 2000/125, and 2250/125 mg of amoxicillin and potassium clavulanate, respectively. A preferred dosage is 12000/125 mg of amoxicillin and potassium clavulanate.

The unit dosage of a modified release formulation according to the present invention may conveniently be provided as a number of swallow tablets or capsules, for instance two, three or four, some of which may be the same and some of which may comprise amoxicillin only and no potassium clavulanate. Thus, for instance, a dosage of 2000 mg amoxicillin and 125 mg potassium clavulanate may be provided by two tablets each comprising 1000/62.5 mg amoxicillin/potassium clavulanate, one tablet comprising 1000 mg of amoxicillin and one tablet comprising 1000/125 mg amoxicillin/potassium clavulanate, two tablets each comprising 500 mg amoxicillin and one tablet comprising 1000/125 mg amoxicillin/potassium clavulanate or four tablets each comprising tablet 500/32.25 mg amoxicillin/potassium clavulanate. In addition, a dosage of 1750 mg amoxicillin and 125 mg potassium clavulanate may be provided by two tablets each comprising 875/62.5 mg amoxicillin/potassium clavulanate or one tablet comprising 875 mg of amoxicillin and one tablet comprising 875/125 mg amoxicillin/potassium clavulanate.

The dosage in a modified release formulation may be may also provided as a single tablet. Because of the quantities of drug substance being used, this would preferably be other than a swallow tablet, for instance a dispersible tablet or a chewable tablet which may also be effervescent and/or dispersible. The unit dosage may also be conveniently provided as a single dosage sachet or as granules, for direct ingestion, for instance on a spoon or after sprinkling on food. It will be appreciated that the unit dosage may also be provided as a number of smaller non-swallow tablets or sachets, for instance 2×1000/62.5 mg or 4×500/32.25 mg amoxicillin/potassium clavulanate.

The unit dosage of the present invention is typically provided either as two smaller units each of which provides half the unit dosage or a single formulation which provides the whole of the unit dosage. Accordingly, in a further aspect, the present invention provides a pharmaceutical formulation of amoxicillin and potassium clavulanate which comprises from 50 to 75 mg of potassium clavulanate and from 850 to 1250 mg of amoxicillin or from 100 to 150 mg of potassium clavulanate and from 1700 to 2500 mg of amoxicillin; which formulation is a modified release formulation comprising an immediate and a slow release phase and in which all of the potassium clavulanate and from 0 to 60% of the amoxicillin is in an immediate release phase and from 40 to 100% of the amoxicillin is in a slow release phase; such that the parameter mean T>MIC is at least 4 h for an MIC of 8 μg/ml.

Typically, the formulation comprises about 62.5 mg of potassium clavulanate and from 950 to 1125, typically about 1000 mg of amoxicillin; or about 125 mg of potassium clavulanate and from 1900 to 2250, typically about 2000 mg of amoxicillin.

Preferably, the slow release phase comprises from 60 to 90, more preferably 70 to 90, yet more preferably 76 to 90% of the total amoxicillin content.

Preferably, T>MIC is at least 4.2, 4.4, 4.6, 4.8 h.

It will be appreciated that the smaller (half) units will typically be a swallow tablet whilst the larger units will typically be a chewable or dispersible tablet or a single dose sachet.

Preferably, the mean plasma concentration of amoxicillin and the mean maximum plasma concentration of amoxicillin are measured after oral administration of a formulation comprising amoxicillin at the start of a meal.

The term "amoxicillin" is used generically to refer to amoxicillin or an alkaline salt thereof, in particular amoxicillin trihydrate and (crystallised) sodium amoxicillin, without distinction and unless otherwise indicated.

Unless otherwise indicated, weights of amoxicillin and (potassium) clavulanate refer to the equivalent weights of the corresponding free acids. In addition, it will be appreciated that in practice, weights of amoxicillin and clavulanate to be incorporated into a formulation will be further adjusted, in accord with conventional practice, to take account of the potency of the amoxicillin and clavulanate.

As used herein, the term "immediate release" refers to the release of the majority of the active material content within a relatively short time, for example within 1 hour, preferably within 30 minutes, after oral ingestion. Examples of such immediate release formulations include conventional swallow tablets, dispersible tablets, chewable tablets, single dose sachets and capsules.

As used herein, the term "slow release" refers to the gradual but continuous or sustained release over a relatively extended period of the active material content (in this case amoxicillin) after oral ingestion and which starts when the formulation reaches the stomach and starts to disintegrate/dissolve. The release will continue over a period of time and may continue through until and after the formulation reaches the intestine. This can be contrasted with the term "delayed release" in which release of the active does not start immediately the formulation reaches the stomach but is delayed for a period of time, for instance until when the formulation reaches the intestine when the increasing pH is used to trigger release of the active from the formulation.

Preferably, the modified release formulation has a biphasic profile in vivo with respect to amoxicillin, that is an initial burst from the immediate release phase to provide an acceptable $C_{max}$ value, supplemented by a further contribution from the slow release phase, to extend the T>MIC parameter to an acceptable value.

Preferably, the modified release formulation provides an "Area Under the (plasma concentration versus time) Curve" (AUC) value which is substantially similar to, for instance at least 80%, preferably at least 90%, more preferably about 100%, of that of the corresponding dosage of amoxicillin taken as a conventional (immediate release) formulation, over the same dosage period, thereby maximising the absorption of the amoxicillin component from the slow release component.

The pharmcokinetic profile for a dosage of the present invention may be readily determined from a single dosage bioavailability study in human volunteers. Plasma concentrations of amoxicillin may then be readily determined in blood samples taken from patients according to procedures well known and documented in the art.

Preferably, the modified release formulations of the present invention are formulated such that the release of amoxicillin is effected predominantly through the stomach and small intestine, so that absorption through the specific amoxicillin absorption site in the small intestine is maximised. Preferably, the amoxicillin release profile is made up of a contribution from an immediate release component which is then complemented and extended by an on-going contribution from a slow release component. Preferably, potassium clavulanate is released substantially immediately from the formulation, when the formulation reaches the stomach and is absorption begins immediately, thereby minimising the risk of degradation from prolonged exposure to the stomach. Such formulations are preferably formulated such that the release of amoxicillin and potassium clavulanate occurs predominantly within 3 hours of ingestion of the formulation.

Preferably, the modified release formulation is a tablet. Representative modified release tablets comprise about 62.5 mg of potassium clavulanate in the immediate release phase, from 0 to 500 mg amoxicillin in the immediate release phase and from 500 to 1000 mg amoxicillin in the slow release phase, for instance:

(a) a tablet comprising 1000 mg amoxicillin and 62.5 mg potassium clavulanate, in which the immediate release phase comprises 62.5 mg±5% of potassium clavulanate and 250 mg±5% amoxicillin and the slow release phase comprises 750 mg±5% of amoxicillin; or (b) a tablet comprising 875 mg amoxicillin and 62.5 mg potassium clavulanate, in which the immediate release phase comprises 62.5 mg±5% of potassium clavulanate and 275 mg±5% amoxicillin, and the slow release phase about 600 mg of amoxicillin.

It will be appreciated that when the unit dose is provided as a single unit, for instance a chewable tablet or a single dose sachet, such unit will comprise twice the above quantities.

For a tablet formulation, the immediate and slow release phases may be provided in a number of different formats.

In a preferred aspect, the immediate and slow release phases are provided as separate layers of a layered tablet.

Accordingly, in a further aspect, the present invention provides for a layered tablet formulation comprising potassium clavulanate and amoxicillin in an immediate release layer phase and amoxicillin in a slow release layer. The layered tablet may have two layers, or two layers plus one or more barrier layer, as well as a coating layer. As used herein, the term "bilayer" tablet refers to a tablet consisting of an immediate release and a slow release layer, optionally with a coating layer.

An immediate release layer may be, for example, a layer which disintegrates immediately or rapidly and has a composition similar to that of known tablets which disintegrate immediately or rapidly. For example, the layer may comprise, in addition to the active material content, excipients including diluents such as microcrystalline cellulose; disintegrants such as cross-linked polyvinylpyrrolidone (CLPVP), sodium starch glycollate; compression aids such as colloidal silicon dioxide and microcrystalline cellulose; and lubricants such as magnesium stearate. Such an immediate release layer may comprise around 60 to 85% (all percentages given herein are on a weight percentage basis unless otherwise stated), preferably 70 to 85%, of active material content, around 10 to 30%, preferably 10 to 20% of fillers/compression aids, and conventional amounts of disintegrants and lubricants, typically about 0.5 to 3%, etc.

An alternative type of immediate release layer may be a swellable layer having a composition which incorporates polymeric materials which swell immediately and extensively in contact with water or aqueous media, to form a water permeable but relatively large swollen mass. Active material content may be immediately leached out of this mass.

Slow release layers have a composition which comprises amoxicillin together with a release retarding excipient which allows for slow release of amoxicillin. Suitable release retarding excipients include pH sensitive polymers, for instance polymers based upon methacrylic acid copolymers such as the Eudragit (trade mark) polymers, for example Eudragit L (trade mark) which may be used either alone or with a plasticiser; release-retarding polymers which have a high degree of swelling in contact with water or aqueous media such as the stomach contents; polymeric materials which form a gel on contact with water or aqueous media; and polymeric materials which have both swelling and gelling characteristics in contact with water or aqueous media.

Release retarding polymers which have a high degree of swelling include, inter alia, cross-linked sodium carboxymethylcellulose, cross-linked hydroxypropylcellulose, high-molecular weight hydroxypropylmethylcellulose, carboxymethylamide, potassium methacrylatedivinylbenzene co-polymer, polymethylmethacrylate, cross-linked polyvinylpyrrolidone, high-molecular weight polyvinylalcohols etc.

Release retarding gellable polymers include methylcellulose, carboxymethylcellulose, low-molecular weight hydroxypropylmethylcellulose, low-molecular weight polyvinylalcohols, polyoxyethyleneglycols, non-cross linked polyvinylpyrrolidone, xanthan gum etc.

Release retarding polymers simultaneously possessing swelling and gelling properties include medium-viscosity hydroxypropylmethylcellulose and medium-viscosity polyvinylalcohols.

A preferred release-retarding polymer is xanthan gum, in particular a fine mesh grade of xanthan gum, preferably pharmaceutical grade xanthan gum, 200 mesh, for instance the product Xantural 75 (also known as Keltrol CR, Trade Mark, Monsanto, 800 N Lindbergh Blvd, St Louis, Mo. 63167, USA). Xanthan gum is a polysaccharide which upon hydration forms a viscous gel layer around the tablet through which the active has to diffuse. It has been shown that the smaller the particle size, the slower the release rate. In addition, the rate of release of drug substance is dependent upon the amount of xanthan gum used and can be adjusted to give the desired profile. Controlled release formulations comprising from 7.5 to 25% xanthan gum are described in EP 0 234 670-A (Boots Co plc). The preferred embodiment is a tablet comprising ibuprofen as the drug substance and 15–20% xanthan gum, which is taken once daily.

Examples of other polymers which may be used include Methocel K4M (Trade Mark), Methocel E5 (Trade Mark), Methocel ES0 (Trade Mark), Methocel E4M (Trade Mark), Methocel K15M (Trade Mark) and Methocel K100M (Trade Mark). An example of a suitable polymer mixture is a mixture of Methocel E5 and K4M, for example 1:1, w:w.

Other known release-retarding polymers which may be incorporated include hydrocolloids such as natural or synthetic gums, cellulose derivatives other than those listed above, carbohydrate-based substances such as acacia, gum tragacanth, locust bean gum, guar gum, agar, pectin, carageenin, soluble and insoluble alginates, carboxypolymethylene, casein, zein, and the like, and proteinaceous substances such as gelatin.

Such a slow release layer may contain polymers which immediately swell in contact with water or aqueous media so that they form a relatively large swollen mass which is not immediately discharged from the stomach into the intestine.

The slow release layer may also include diluents such as lactose; compression aids such as microcrystalline cellulose; and lubricants such as magnesium stearate. The slow release layer may further comprise disintegrants, such as cross-linked polyvinylpyrrolidone (CLPVP) and sodium starch glycollate; binders such as povidone (polyvinylpyrrolidone); desiccants, such as silicon dioxide; and soluble excipients such as mannitol or other soluble sugars. Typically, the slow release layer comprises from about 60 to 80% by weight of amoxicillin; from 10 to 20% by weight of diluent/compression aid and from 1 to 2.5% by weight of lubricant.

When xanthan gum is used as release-retarding polymer, the layer contains from 60 to 80% of amoxicillin, from 4 to 25%, preferably 4 to 15%, more preferably 5 to 15%, typically about 6 to 10%, of xanthan gum, from 10 to 30%, preferably 10 to 20% of fillers/compression aids, and conventional quantities of lubricants, all % being by weight of the layer. In a preferred embodiment, the slow release layer comprises from 70 to 80% of amoxicillin, from 5 to 10%, of xanthan gum, from 10 to 20% of microcrystalline cellulose, and from 1 to 2.5% of magnesium stearate, all % being by weight of the layer.

When release-retarding polymers other than xanthan gum are used, the slow release layer may contain around 30 to 70%, preferably from 40 to 60%, of amoxicillin, from 15 to 45% of release-retarding polymer, from 0 to 30% of fillers/compression aids, conventional quantities of lubricants, and from 5 to 20% of soluble excipients, all % being by weight of the layer.

A further release retarding excipient for use when the amoxicillin in the slow release layer is in the form of a soluble salt thereof, such as sodium or potassium amoxicillin, is an organic acid.

Preferably, the organic acid is a pharmaceutically acceptable organic acid present in a molar ratio of from 100:1 to 1:10, preferably 50:1 to 1:5, more preferably 20:1 to 1:2 (amoxicillin to organic acid).

It is believed that intimate contact between the organic acid and the salt of amoxicillin in the pharmaceutical formulation, for instance as a consequence of compacted granule formation or direct compression in a tablet, causes some form of interaction which modifies the release of the amoxicillin component from the formulation.

Soluble pharmaceutically acceptable salts of amoxicillin include alkali metal salts such as sodium and potassium; alkaline earth metal salts such as magnesium and calcium, and acid salts such as amoxicillin hydrochloride. Preferably, the salt is sodium amoxicillin, more preferably crystallised sodium amoxicillin.

As used herein, the term "pharmaceutically acceptable organic acid" refers to organic acids which are without pharmacological effect per se, have acceptable organo-leptic properties, have acceptable density, do not have an extreme pH and are preferably solid. Examples thereof include mono-carboxylic acids and poly-carboxylic acids having from 2 to 25, preferably from 2 to 10, carbon atoms; monocyclic and polycyclic aryl acids such as benzoic acid; as well as monohydrogen, dihydrogen etc metal salts of multi-valent acids. A single pharmaceutically acceptable organic acid may be used, or two or more of such may be used in combination. Preferably, the organic acid is a $C_{(2-10)}$alkyl- or alkenyl-carboxylic acid having from one, two or three carboxylic acid groups, and optionally with one or more hydroxy substituents or an additional CO group in the carbon chain, for instance malonic acid, succinic acid, fumaric acid, maleic acid, adipic acid, lactic acid, levulinic acid, sorbic acid or a fruit acid such as tartaric acid, malic acid, ascorbic acid or citric acid, or an acidic salt thereof, more preferably citric acid, in particular anhydrous citric acid.

The organic acid may be used alone or in combination with a release retarding polymer as hereinbefore described. A preferred combination comprises citric acid and a release retarding gellable polymer, in particular xanthan gum. In the presence of the organic acid, for instance citric acid, xanthan gum may be used at a lower level then when included on its own, for instance, from 0.5 to 8%, preferably 1 to 5%, typically about 2%, by weight of the slow release layer.

When an organic acid is used as a release-retarding excipient, the slow release layer contains from 60 to 80% of a soluble salt of amoxicillin, from 10 to 30%, preferably 10 to 20% of fillers/compression aids, and conventional quantities of lubricants, all % being by weight of the layer. In a preferred embodiment, the slow release layer comprises from 60 to 70% of a soluble salt of amoxicillin, from 10 to 20% of microcrystalline cellulose, and from 1 to 2.5% of magnesium stearate, all % being by weight of the layer.

In a representative example, a layered tablet comprises in the slow release layer crystallised sodium amoxicillin and citric acid, in a molar ratio of about 50:1 to 1:2, preferably 20:1 to 1:2, more preferably 2:1 to 1:1.2, yet more preferably about 1:1. In a representative embodiment, the slow release layer comprises 750 mg±5% crystallised sodium amoxicillin, and about 134 mg±10% citric acid.

In a representative layered tablet comprising 1000 mg amoxicillin and 62.5 mg potassium clavulanate, the immediate release layer comprises 250 mg±5% amoxicillin, preferably amoxicillin trihydrate, and about 62.5 mg±5% of potassium clavulanate and the slow release layer 750 mg±5% of amoxicillin, preferably crystallised sodium amoxicillin, and 134 mg±10% citric acid.

The tablet formulations of the invention may also include one or more barrier layers, which may be located between the respective first and second layers, and/or on one or more of the outer surfaces of the first and second layers, for example the end faces of the layers of a substantially cylindrical tablet. Such barrier layers may, for example, be composed of polymers which are either substantially or completely impermeable to water or aqueous media, or are slowly erodable in water or aqueous media or biological liquids and/or which swell in contact with water or aqueous media. Suitably the barrier layer should be such that it retains these characteristics at least until complete or substantially complete transfer of the active material content to the surrounding medium.

Suitable polymers for the barrier layer include acrylates, methacrylates, copolymers of acrylic acid, celluloses and derivatives thereof such as ethylcelluloses, cellulose acetate propionate, polyethylenes and polyvinyl alcohols etc. Barrier layers comprising polymers which swell in contact with water or aqueous media may swell to such an extent that the swollen layer forms a relatively large swollen mass, the size of which delays its immediate discharge from the stomach into the intestine. The barrier layer may itself contain active material content, for example the barrier layer may be a slow or delayed release layer. Barrier layers may typically have an individual thickness of 2 mm to 10 microns.

Suitable polymers for barrier layers which are relatively impermeable to water include the Methocel (trade mark) series of polymers mentioned above, for example Methocel K100M, Methocel K15M, Methocel E5 and Methocel E50, used singly or combined, or optionally combined with an Ethocel (trade mark) polymer. Such polymers may suitably be used in combination with a plasticiser such as hydrogenated castor oil. The barrier layer may also include conventional binders, fillers, lubricants and compression acids etc such as Polyvidon K30 (trade mark), magnesium stearate, and silicon dioxide, e.g. Syloid 244 (trade mark).

The tablet formulation of the invention may be wholly or partly covered by a coating layer, which may be a protective layer to prevent ingress of moisture or damage to the tablet. The coating layer may itself contain active material content, and may, for example, be an immediate release layer, which immediately disintegrates in contact with water or aqueous media to release its active material content, for example amoxicillin and potassium clavulanate. Preferred coating materials comprise hydroxypropylmethylcellulose and polyethylene glycol, with titanium dioxide as an opacifying agent, for instance as described in WO 95/28927 (SmithKline Beecham).

As well as active material content etc, the tablet of the invention may also include a pH modifying agent, such as a pH buffer, which may be contained in either the immediate-, or slow-release layers, or in a coating around all or part of the tablet. A suitable buffer is calcium hydrogen phosphate.

In a tablet without a barrier layer, the immediate release layer comprises from 50 to 60% and the slow release layer comprises from 40 to 50% of the overall tablet weight. When a barrier layer is present, the immediate release layer typically comprises from 40 to 50%, the slow release layer comprises from 35 to 45%, and the barrier layer comprises from 5 to 20% of the overall tablet weight.

It is found that a satisfactory pharmacokinetic profile may be obtained from a bilayered tablet of the present invention without the need to include a barrier layer. Accordingly, a bi-layer tablet is preferred. This also reduces the complexity of the manufacturing process.

It will be appreciated that layered tablets having an immediate release layer and a slow release layer as hereinbefore described are novel. Accordingly, in a further aspect, the present invention provides for a pharmaceutical layered tablet formulation comprising an immediate release layer and a slow release layer and comprising from 700 to 1250 mg, typically 1000 mg, amoxicillin, and from 50 to 75 mg, typically 62.5 mg, potassium clavulanate, such that all the potassium clavulanate and from 0 to 60% of the amoxicillin is in the immediate release layer and from 40 to 100% of the amoxicillin is in the immediate release layer, in combination with pharmaceutically acceptable excipients or carriers. Preferably, the layered tablet is a bi-layered tablet.

Suitably the tablet formulations of the invention may be formed by known compression tabletting techniques, for example using a known multi-layer tabletting press. Preferably, in a preliminary step, slugging or roller compaction is used to form granulates. Lubricants and compression aids (if used) are then added, to form a compression blend for subsequent compaction.

Representative bilayer tablets of the present invention may be made by a process which comprises, as an early phase, the formation of slow release compacted granules, comprising the steps of milling sodium amoxicillin, a portion of the diluent/compression aid such as microcrystalline cellulose (typically about 30%), a portion of the lubricant (typically about 70%) and a pharmaceutically acceptable organic acid such as a fruit acid, for instance citric acid, and then blending with a release retarding polymer such as xanthan gum, if present, and a compression aid such as colloidal silicon dioxide, compacting the blend, for instance in a roller compactor or by slugging, and then milling, to form slow release granules. Preferably such granules have a size in the range 100 to 1000 microns. The incorporation of xanthan gum appears to also have an unexpected benefit on processability.

Alternatively, slow release granules in which amoxicillin is present as amoxicillin trihydrate and the release modifying excipient is xanthan gum may be prepared by a similar process.

Such slow release compacted granules may then be blended with other excipients such as the remaining magnesium stearate and microcrystalline cellulose, to form a slow release compression blend.

In addition, amoxicillin trihydrate, potassium clavulanate (preferably as 1:1 blend with microcrystalline cellulose), microcrystalline cellulose (a portion of total used), are milled and blended with a lubricant such as magnesium stearate (preferably about 50% of the total), and then compacted, for instance in a roller compactor or by slugging, and milled to form immediate release compacted granules. These immediate release compacted granules may then be blended with other excipients such as the remaining magnesium stearate and microcrystalline cellulose (about 13%), a compression aid such as colloidal silica, and a disintegrant such as sodium starch glycollate, to form an immediate release compression blend.

The immediate release and slow release compression blends may then be compressed as separate layers on a bilayer tablet press, to form bilayer tablets.

Such slow release granules are novel. Accordingly, in a further aspect, the present invention provides for compacted granules comprising a soluble salt of amoxicillin, for instance sodium amoxicillin, a diluent/compression aid, and an organic acid or a release retarding polymer or a mixture thereof, as hereinbefore defined. In a yet further aspect, the present invention also provides for compacted granules comprising amoxicillin, for instance amoxicillin trihydrate or sodium amoxicillin, a diluent/compression aid, and a release retarding polymer, for instance xanthan gum.

Alternatively, a dry densification process may be used, e.g. briquetting. Typically the active material content, pH modifiers, buffers, fillers and/or diluent, release retarding agents, disintegrants and binders, when used are mixed, then lubricants and compression aids are added. The complete mixture may then be compressed under high pressure in the tablet press. A wet granulation process may be also be used, for instance with isopropanol as the solvent and Polyvidon K-30 (trade mark) as the wet granulating aid.

A barrier layer, if present, may typically be made up by a wet granulation technique, or by dry granulation techniques such as roller compaction. Typically the barrier material, e.g. Methocel (trade mark) is suspended in a solvent such as ethanol containing a granulation acid such as Ethocel or Polyvidon K-30 (trade mark), followed by mixing, sieving and granulation. Typically a first layer may be formed, then a barrier layer deposited upon it, e.g. by compression, spraying or immersion techniques, then the second layer may be formed so that the barrier layer is sandwiched between the first and second layers. Additionally, or alternatively, the first and second layers may be formed and a barrier layer may then be formed, for instance by compression, spraying or immersion, on one or more of the end faces of the tablet.

A process for the preparation of crystallised sodium amoxicillin is described in EP-A-0 131 147 (Beecham Group plc).

Potassium clavulanate is known to be extremely water sensitive. Therefore tablet formulations which contain potassium clavulanate should be made up in dry conditions, preferably at 30% relative humidity or less, and the ingredients of the formulation should be pre-dried where appropriate. Tablet formulations of the invention should be stored in containers which are sealed against the ingress of atmospheric moisture.

Tablet cores may then be coated with a coating layer which may be applied form an aqueous or an organic solvent system, preferably an aqueous solvent system, to provide film coated tablets.

The invention also provides a method for the manufacture of a tablet formulation as described above comprising the steps of forming said first and second layers, and any barrier layers and coating layer(s) which may be present.

In addition to the layered tablet approach hereinbefore described, other types of tablet may be used to provide an immediate release phase and a slow release phase, using the excipients hereinbefore described but providing the phases in different formats. Thus, the slow release phase may form the core of a tablet which is then surrounded by an outer casing forming the immediate release phase, optionally with an intermediate coating layer around the core and/or a final coating layer around the outer casing (see WO 95/28148, SmithKline Beecham). The slow release phase may also be provided as granules which are dispersed in a matrix of amoxicillin and potassium clavulanate, the matrix forming the immediate release phase (see WO 96/04908, SmithKline Beecham).

In a further variant, a monolith modified release tablet may be prepared from slow release compacted granules comprising amoxicillin, a diluent/compression aid such as microcrystalline cellulose, and a pharmaceutically acceptable organic acid such as a fruit acid, for instance citric acid (if amoxicillin is present as a soluble salt thereof), or a release retarding polymer such as xanthan gum or a mixture thereof, preferably a release retarding polymer (as hereinbefore described); and immediate release compacted granules comprising amoxicillin and potassium clavulanate (as hereinbefore described) or immediate release compacted granules comprising amoxicillin and potassium clavulanate, for instance in a 2:1 ratio, and further immediate release compacted granules comprising amoxicillin (as described in WO 98/35672, SmithKline Beecham Laboratoires Pharmaceutiques), the granules being combined with extragranular excipients to form tablets. Such granules may also be processed into other pharmaceutical formulations, for instance single dosage sachets, capsules or chewable tablets comprising a unit dosage as hereinbefore described.

Chewable tablets according to the present invention typically comprise a chewable base formed from, for instance, mannitol, sorbitol, dextrose, fructose or lactose alone or in combination. A chewable tablet may also comprise further excipients, for instance, disintegrants, lubricants, sweetening agents, colouring and flavouring agents. Such further excipients together will preferably comprise from 3 to 10%, more preferably 4 to 8%, yet more preferably 4 to 7% by weight of the tablet. Disintegrants may be present in from 1 to 4%, preferably from 1 to 3%, more preferably from 1 to 2% by weight of the tablet. Representative disintegrants include crospovidone, sodium starch glycollate, starches such as maize starch and rice strach, croscarmellose sodium and cellulose products such as microcrystalline cellulose, microfine cellulose, low substituted hydroxy propyl cellulose, either used singly or in admixture. Preferably, the disintegrant is crospovidone. Lubricants may be present in from 0.25 to 2.0%, preferably from 0.5 to 1.2% by weight of the tablet. Preferred lubricants include magnesium stearate. Preferably, the sweetening agent is an artificial sweetening agent such as sodium saccharin or aspartame, preferably aspartame, which may be present in from 0.5 to 1.5% by weight of the tablet. Preferably, a tablet of the present invention is substantially free of sugar (sucrose). Preferred flavouring agents include fruit flavours which may be natural or synthetic, for instance peppermint, cherry and banana, or a mixture thereof.

Single dose sachets according to the present invention comprise, in addition to the drug substance, excipients typically included in a sachet formulation, such as a sweetener, for instance aspartame, flavourings, for instance fruit flavours, optionally a suspending agent such as xanthan gum, as well as silica gel, to act as a desiccant.

Capsules according to the present invention comprise, in addition to the drug substance, excipients typically included in a capsule, for instance starch, lactose, microcrystalline cellulose, magnesium stearate. It will be appreciated that due to the hygroscopic nature of clavulanate, the use of materials such as gelatin for forming the capsules should be avoided. Preferably, capsules are prepared from materials such as HPMC or a gelatin/PEG combination.

In a further embodiment, the slow release phase may be provided as a separate component, for instance as a separate tablet, so that the unit dosage is provided as a combination of a conventional component in which amoxicillin and potassium clavulanate are released immediately, optionally with a conventional amoxicillin formulation such as a tablet, and a further formulation, for instance a tablet, comprising amoxicillin (and no potassium clavulanate) from which amoxicillin is released slowly. The weight of potassium clavulanate and the combined weights of amoxicillin in the conventional and slow release formulations will provide the overall unit dosage. Thus, for instance a dosage of 2000/125 mg may be provided by a combination of an existing 250/125 mg amoxicillin/potassium clavulanate tablet and in combination with 2 slow release tablet comprising 875 mg of amoxicillin, respectively. Furthermore, a dosage of 1750/125 mg may be provided by an existing 875/125 mg tablet (as described in WO 95/28927, SmithKline Beecham) in combination with a slow release tablet comprising 875 mg of amoxicillin. Accordingly, in a further aspect, the present invention provides for a kit comprising a conventional (immediate release) tablet comprising amoxicillin and potassium clavulanate, optionally with a conventional (immediate release) tablet comprising amoxicillin, and a slow release tablet comprising amoxicillin (and no potassium clavulanate).

Representative slow release amoxicillin tablets are described in PCT/IB00/00992.

Preferably, the unit dosage forms of the present invention are packaged in containers that inhibit the ingress of atmospheric moisture, for instance blister packs, tightly closed bottles or desiccated pouch packs etc which are conventional in the art. Preferably, bottles also include a desiccating material, to preserve the clavulanate. Preferred bottles include HDPE bottles. Preferred blister packs include cold-formed blister packs in which each blister may contain one tablet, or two tablets, where the unit dosage is two tablets, for instance 2×1000/62.5 mg tablets, to improve patient compliance. Formulations of the present invention are of use in treating bacterial infections. Accordingly, in a further aspect, the present invention provides for a method of treating a bacterial infection in a patient in need thereof which method comprises administering an effective amount of a formulation as hereinbefore defined, to a patient in need thereof, once daily, preferably about every 24 h.

Infections amenable to treatment by the present method include those caused by the commonly occurring β-lactamase producing respiratory pathogens, most notably *H influenzae* and *M catarrhalis,* such as respiratory tract infections, including community acquired pneumoniae (CAP), acute exacerbations of chronic bronchitis (AECB) and acute bacterial sinusitis (ABS). In addition, the present invention will be useful for treating infections caused by *S pneumoniae* (including resistant *S pneumoniae*). Most outpatient respiratory infections are caused by either *S pneumoniae* and/or the β-lactamase producing bacteria and are treated empirically so there is a continuing need for a method of treatment, such as the present invention, that provides a spectrum of activity that covers all such pathogens. The duration of therapy will generally between 7 and 14 days, typically 7 days for indications such as acute exacerbations of chronic bronchitis but 10 days for acute bacterial sinusitis. Typically, the dosages regimens are designed for adult patients, rather than paediatric patients.

The modified release formulations of the present invention are intended for use in a bid dosing regimen. It will be appreciated that whilst such a bid dosing regimen is recognised to offer the advantage of greater convenience and therefore likely greater compliance, in some instances, it may be preferred to use administer the same total daily dosage but in a tid regimen, that is in equally divided doses every 8 hours, rather than every 12 hours.

Accordingly, in a further aspect, the present invention provides a unit dosage of amoxicillin and potassium clavulanate which comprises from 100 to 150 mg of potassium clavulanate and from 1200 to 1700 mg of amoxicillin; which formulation is a modified release formulation comprising an immediate and a slow release phase and in which all of the potassium clavulanate and from 0 to 50% of the amoxicillin is in an immediate release phase and from 50 to 100% of the amoxicillin is in a slow release phase; such that the mean T>MIC is at least 2.6 h for an MIC of 8 $\mu$g/ml.

Typically, the unit dosage comprises about 125 mg of potassium clavulanate.

Preferably, the unit dosage comprises from 1250 to 1500, typically about 1350 mg of amoxicillin.

Preferably, the slow release phase comprises from 60 to 90, more preferably 70 to 90, yet more preferably 76 to 90% of the total amoxicillin content.

Preferably, the mean T>MIC is at least 2.8, 3.0, 3.2 h.

Representative unit dosages include 1350/125, and 750/125 mg of amoxicillin and potassium clavulanate, respectively. A preferred dosage is 675/125 mg of amoxicillin and potassium clavulanate.

Such a dosage may be provided by one or two modified release pharmaceutical formulations, in particular two bilayer or monolith swallow tablets each comprising half the dosage (for instance, 600 to 850 mg amoxicillin, more preferably 625 to 750 mg amoxicillin, and 62.5 mg potassium clavulanate) or a larger chewable tablet or single dose sachet comprising the entire unit dosage (for instance, 1200 to 1700 mg amoxicillin, more preferably 1250 to 1500 mg amoxicillin, and 125 mg potassium clavulanate), by appropriate adjustment to the corresponding formulations hereinbefore described. A representative tablet comprises 750 mg of amoxicllin and 62.5 mg of potassium clavulanate, having a nominal ratio of amoxicllin:potassium clavulanate of 12:1. Such a tablet may comprise from 300 to 450 mg of amoxicillin in the immediate release phase and from 300 to 450 mg of amoxicllin in the slow release phase, to make a total of 750 mg amoxicillin. A further representative tablet comprises 675 mg of amoxicllin and 62.5 mg of potassium clavulanate. Such a tablet may comprise from 250 to 400 mg of amoxicillin in the immediate release phase and from 250 to 400 mg of amoxicllin in the slow release phase, to make a total of 675 mg amoxicillin.

It will be appreciated that the methods and formulations hereinbefore described for amoxicillin and clavulanate are also applicable to amoxicillin alone, with no clavulanate, particularly for treating infections where β-lactamase producing pathogens are not implicated, for instance infections caused by the organism *Streptococcus pyogenes,* such acute bacterial tonsillitis and/or pharyngitis. The present invention also all such uses and formulations of amoxicillin as the sole agent.

The invention will now be described by way of example only with reference to the accompanying drawings, in which:

FIG. 1 shows the structure of various types of layered tablets of the present invention, in particular the structure of substantially cylindrical compressed tablets are shown in longitudinal section.

In FIG. 1A, the tablet comprises a first layer (1) and a second layer (2), without any barrier layer or coating layer.

In FIG. 1B, the tablet comprises a first layer (1), a second layer (2), and a barrier layer (3) sandwiched between the first and second layers (1) and (2).

In FIG. 1C, the tablet comprises a first layer (1), a second layer (2), and a barrier layer (3) located on the end face of the second layer (2).

In FIG. 1D, the tablet comprises a first layer (1), a second layer (2), a barrier layer (3) sandwiched between the first and second layers (1) and (2), and a coating layer (4) which partly covers the tablet. The dotted line shows the possibility of the coating layer (4A) covering the entire tablet.

In FIG. 1E, the tablet comprises a first layer (1) a second layer (2), and a third layer (3) intermediate between the first and second layers (1) and (2). All three of these layers (1), (2) and (3) include active material content.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

EXAMPLE 1

1000 mg Monolith Tablet

| | mg/tablet | % |
|---|---|---|
| Crystallised Sodium Amoxicillin[1] | 824.2 | 51.51 |
| Amoxicillin Trihydrate[2] | 290.7 | 18.17 |
| Clavulanate Potassium[3] | 76.2 | 4.76 |
| Dried Microcrystalline Cellulose | 165.9 | 10.37 |
| Magnesium Stearate | 23.0 | 1.44 |
| Sodium Starch glycollate | 80.0 | 5.00 |
| Colloidal silicon dioxide | 6.3 | 0.39 |
| Citric acid | 133.7 | 8.36 |
| Total | 1600 | 100.0 |

[1] adjusted for potency of the amoxicillin component and corresponding to 750 mg of amoxicillin
[2] adjusted for potency of the amoxicillin component and corresponding to 250 mg of amoxicillin
[3] adjusted for potency of the clavulanate potassium component and corresponding to 62.5 mg of clavulanate potassium Two separate batches of granules, the first, immediate release granules, comprising amoxicillin and potassium clavulanate and the second, slow release granules, comprising sodium amoxicillin and citric acid, were prepared by roller compaction and then combined with the remaining excipients, blended and formed into tablets in a tablet press.

In further detail, immediate release granules were prepared thus: containers were charged with dried microcrystalline cellulose (1), amoxicillin trihydrate (2) and (5) (in 1:1 ratio), a potassium clavulanate/dried microcrystalline cellulose blend (1:1) and magnesium stearate (about 50% of total) (4). The contents of containers (1) and (2) were passed through a mesh, milled in a "Fitzmill" operating at 1500 rpm and blended with the contents of container (3). The contents of container (4) were then screened and milled and blended with the initial blend and then blended with the contents of container (5) which had gone through a preliminary screening and milling step. This blend was then subjected to roller compaction using a Chilsonator operating at a pressure of 1000 psi±200 psi and the product milled and screened through a vibratory screen with 14 and 80 meshes, to provide immediate release granules.

Slow release granules were prepared thus: containers were charged with dried microcrystalline cellulose (about 70%) and anhydrous citric acid (1), sodium amoxicillin (2) and (4) (in a 1:1 ratio), and magnesium stearate (about 70%), colloidal silicon dioxide and xanthan gum (3). The contents of containers (1) and (2) were screened and milled in a Fitzmill, and then blended with the contents of container (3), blended and then the contents of container (4) which had been milled and screened in a preliminary step. This blend was subjected to roller compaction on a chilsonator, operating at a pressure of 600 psi±100 psi, milled and screened, to provide slow release granules.

The immediate release and slow release granules were blended with the remaining excipients (magnesium stearate, dried microcrystalline cellulose) and then compressed into a monolith tablet on a standard tabletting machine.

Finally, the tablet cores were coated with an aqueous film coating in a 60 inch coating pan, operating on a 300 kg sub-batch. The pan was equipped with 4 spray guns and rotated at 3 to 5 rpm. The inlet air was dehumidified with the temperature in the range 56 to 60° C. whilst the exhaust air humidity was in the range 4 to 12% and the temperature in the range 43 to 50° C. The spray rate was 80 to 120 ml/min/spray gun.

In vivo Pharmacokinetic Evaluation of Formulations

The bioavailability of a dosage according to the present invention may be evaluated in a human volunteer study, typically an open, randomised, crossover studies in healthy volunteers, for instance using the study design described in PCT/IB00/00992.

In a study involving on prototype formulations to provide a unit dosage of 2000 mg amoxicillin and 125 mg potassium clavulanate, a dosage made up of a two monolith tablets according to Example 1, was found to have mean T>MIC of about 4.8 h for an MIC =8 µg/ml (n=11).

The present invention also extends to formulations which are bioequivalent to the tablets the present invention, in terms of both rate and extent of absorption, for instance as defined by the US Food and Drug Administration and discussed in the so-called "Orange Book" (Approved Drug Products with Therapeutic Equivalence Evaluations, US Dept of Health and Human Services, 19th edn, 1999).

Reference Data

The existing Augmentin 875/125 mg tablet has a mean $C_{max}$ value of 11.6±2.8 µg/ml (Physicians Desk Reference, Medical Economics Co, 52 edition, 1998, 2802). The time above MIC was about 40% of the 12 hour dosing interval for an MIC of 2 µg/ml and about 30% for an MIC of 4 µg/ml (SmithKline Beecham data). The existing Augmentin 500/125 mg tablet has a mean $C_{max}$ value of 6.5±1.4 µg/ml (Physicians Desk Reference, Medical Economics Co, 52 edition, 1998, 2802).

What is claimed is:

1. A pharmaceutical formulation which provides a unit dosage of amoxicillin and potassium clavulanate, the formulation comprising in solid form from about 100 to 150 mg of potassium clavulanate and from about 1700 to 2500 mg of amoxicillin;

wherein all of the potassium clavulanate and from 0 to 50% of the amoxicillin are contained in a first release phase; and from 50 to 100% of the amoxicillin is in a second release phase; such that the composition when administered to a human, has a T>MIC is at least 4 hours for an MIC of 8 µg/ml.

2. A formulation according to claim 1 in which the unit dosage comprises about 125 mg of potassium clavulanate.

3. A formulation according to claim 1 in which the unit dosage comprises from 1900 to 2250 mg of amoxicillin.

4. A formulation according to claim 1 in which the unit dosage comprises about 2000 mg of amoxicillin.

5. A formulation according to claim 1 in which the second release phase comprises from 60 to 90% of the total amoxicillin content.

6. A formulation according to claim 1 in which the second release phase comprises from 70 to 90% of the total amoxicillin content.

7. A formulation according to claim 1 in which the second release phase comprises from 76 to 90% of the total amoxicillin content.

8. A formulation according to claim 1 in which mean T>MIC is at least 4.2 hours.

9. A formulation according to claim 1 in which mean T>MIC is at least 4.4 hours.

10. A formulation according to claim 1 in which mean T>MIC is at least 4.6 hours.

11. A formulation according to claim 1 in which mean T>MIC is at least 4.8 hours.

12. A formulation according to claim 1 in which the unit dosage is selected from 1750/125, 2000/125, and 2250/125 mg of amoxicillin and potassium clavulanate, respectively.

13. A formulation according to claim 1 in which the unit dosage is selected from a single monolith tablet, from 2 to 4 monolith tablets, a single bilayered tablet, or from 2 to 4 bilayered tablets.

14. A formulation according to claim 1 in which the unit dosage is provided as 2 tablets comprising about 1000/62.5 mg amoxicillin/potassium clavulanate.

15. A pharmaceutical formulation of amoxicillin and potassium comprising a composition in a solid form of from about 50 to 75 mg of potassium clavulanate and from about 850 to 1250 mg of amoxicillin; or from about 100 to 150 mg of potassium clavulanate and from about 1700 to 2500 mg of amoxicillin wherein all of the potassium clavulanate and from 0 to 60% of the amoxicillin is in a first release phase and from 40 to 100% of the amoxicillin is in a second release phase; which upon administration to a human provides a T>MIC of at least 4 hours for an MIC of 8 βg/ml.

16. A pharmaceutical formulation according to claim 15 which is a layered tablet formulation comprising the first release phase in a first layer, and the second release phase in a second layer.

17. A pharmaceutical formulation according to claim 16 in which the second release layer comprises at least one release retarding excipient selected from pH sensitive polymers; release-retarding polymers which have a high degree of swelling in contact with water or aqueous media such as the stomach contents; polymeric materials which form a gel on contact with water or aqueous media; and polymeric materials which have both swelling and gelling characteristics in contact with water or aqueous media.

18. A pharmaceutical formulation according to claim 17 in which release retarding excipient is xanthan gum present in front about 4 to 15% by weight of the layer.

19. A pharmaceutical formulation according to claim 16 in which the second release layer comprises a pharmaceutically acceptable soluble salt of amoxicillin and at least one pharmaceutically acceptable organic acid which are admixed, as solids, in intimate contact at a ratio of from about 20:1 to about 1:2 (amoxicillin free acid equivalent to organic acid equivalent).

20. A pharmaceutical formulation according to claim 19 in which pharmaceutically acceptable organic acid is a fruit acid.

21. A method of treating a bacterial infection in a patient in need thereof which method comprises administering an effective amount of a formulation according to claim 1 to said patient about every 12 hours.

22. A pharmaceutical formulation according to claim 18 wherein the xanthan gum is present in an amount from about 5% to about 10% by weight of the layer.

23. A pharmaceutical formulation according to claim 19 in which the soluble salt of amoxicillin is sodium amoxycillin.

24. A pharmaceutical formulation according to claim 19 in which the soluble salt of amoxicillin is crystallized sodium amoxycillin.

25. A pharmaceutical formulation according to claim 19 wherein the at least one pharmaceutically acceptable organic acid is selected from pharmaceutically acceptable monocarboxylic acid and polycarboxylic acid having from 2 to 10 carbon atoms and an acidic salt of any of the foregoing.

26. A pharmaceutical formulation according to claim 19 wherein the at least one pharmaceutically acceptable organic acid is selected from $C_{(2-10)}$ alkyl- and $C_{(2-10)}$ alkenyl-carboxylic acids having one, two, or three carboxylic acid groups, and optionally at least one hydroxy substituent, and optionally at least one —CO group in the carbon chain and an acidic salt of any of the foregoing.

27. A pharmaceutical formulation according to claim 26 wherein the at least one pharmaceutically acceptable organic acid is selected from malonic acid, succinic acid, fumaric acid, maleic acid, adipic acid, lactic acid, levulinic acid, sorbic acid, tartaric acid, malic acid, ascorbic acid, citric acid, and an acidic salt of any of the foregoing.

28. A pharmaceutical formulation according to claim 20 wherein the fruit acid is tartaric acid, malic acid, ascorbic acid or citric acid.

29. A pharmaceutical formulation according to claim 20 wherein the fruit acid is citric acid.

30. A pharmaceutical formulation according to claim 20 wherein the fruit acid is anhydrous citric acid.

31. A pharmaceutical formulation according to claim 23 wherein the pharmaceutically acceptable organic acid is citric acid.

32. A pharmaceutical formulation according to claim 23 wherein the pharmaceutically acceptable organic acid is anhydrous citric acid.

33. A pharmaceutical formulation according to claim 24 wherein the fruit acid is citric acid.

34. A pharmaceutical formulation according to claim 24 wherein the fruit acid is anhydrous citric acid.

35. A pharmaceutical formulation according claim 15 wherein the first release phase comprises at least one pharmaceutically acceptable soluable salt of amoxicillin.

36. A pharmaceutical formulation according to claim 35 wherein the soluable salt is amoxicillin trihydrate, or a mixture thereof.

37. A pharmaceutical formulation according claim 15 wherein the the first release phase comprises at least one pharmaceutically acceptable soluble salt of amoxicillin; and the second release phase comprises a soluble salt of amoxicillin and at least one pharmaceutically acceptable organic acid.

38. A pharmaceutical formulation according to claim 37 wherein the soluble salt of amoxicillin in the first release phase is amoxicillin trihydrate, or a mixture thereof.

39. A pharmaceutical formulation as claimed in claim 37 in which the soluable salt of amoxicillin in the second release phase is sodium amoxycillin.

40. A pharmaceutical formulation as claimed in claim 37 which the soluble salt of amoxicillin in the second release phase is crystallized sodium amoxycillin.

41. A pharmaceutical formulation as claimed in claim 37 wherein the at least one pharmaceutically acceptable organic acid is selected from pharmaceutically acceptable monocarboxylic acid and polycarboxylic acid having from 2 to 10 carbon atoms and an acidic salt of any of the foregoing.

42. A pharmaceutical formulation according to claim 37 wherein the at least one pharmaceutically acceptable organic acid is selected from malonic acid, succinic acid, fumaric acid, maleic acid, adipic acid, lactic acid, levulinic acid, sorbic acid, tartaric acid, malic acid, ascorbic acid, citric acid, and an acidic salt of any of the foregoing.

43. A pharmaceutical formulation according to claim 42 wherein the fruit acid is tartaric acid, malic acid, ascorbic acid or citric acid.

44. A pharmaceutical formulation according to claim 42 wherein the fruit acid is citric acid.

45. A pharmaceutical formulation according to claim 15 in which the second release phase comprises from 60% to 90% of the total amoxicillin content.

46. A pharmaceutical formulation according to claim 15 in which the second release phase comprises from 70 to 90% of the total amoxicillin content.

47. A pharmaceutical formulation according to claim 15 in which the second release phase comprises from 76% to 90% of the total amoxicillin content.

48. A pharmaceutical formulation according to claim 15 in which the mean T>MIC is at least 4.2 hours.

49. A pharmaceutical formulation according to claim 15 in which the mean T>MIC is at least 4.4 hours.

50. A pharmaceutical formulation according to claim 15 in which the mean T>MIC is at least 4.6 hours.

51. A pharmaceutical formulation according to claim 15 in which the mean T>MIC is at least 4.8 hours.

52. A pharmaceutical formulation according to claim 17 wherein the at least one release retarding excipient is selected from methylcelluloses, carboxymethylcelluloses, low-molecular weight hydroxypropylmethylcelluloses, low-molecular weight polyvinylalcohols, polyoxyethyleneglycols, and noncross-linked polyvinylpyrrolidones.

53. A pharmaceutical formulation according to claim 15 in which the unit dosage is provided as a single monolith tablet, from 2 to 4 monolith tablets, a single bilayered tablet, or from 2 to 4 bilayered tablets.

54. A pharmaceutical formulation according to claim 15 in which the unit dosage is provided as 2 tablets each comprising 1000/62.5 mg amoxicillin/potassium clavulanate or 4 tablets each comprising 500/33.25 mg amoxicillin/potassium clavulanate.

55. A pharmaceutical formulation according to claim 15 in which the unit dosage comprises from 1900 to 2250 mg of amoxicillin.

56. A pharmaceutical formulation according to claim 55 in which the unit dosage comprises about 2000 mg of amoxicillin.

57. A pharmaceutical formulation according to claim 15 in which the unit dosage is selected from 1750/125, 2000/125, and 2250/125 mg of amoxicillin and potassium clavulanate, respectively.

58. A pharmaceutical formulation according to claim 15 in which the second release phase comprises from 50% to 100% of the total amoxicillin content.

59. A pharmaceutical formulation according to claim 15 in which the first release phase comprises from 0% to 50% of the total amoxicillin content.

60. A pharmaceutical formulation according to claim 19 wherein the ratio of amoxicillin free acid equivalent to organic acid equivalent in the second phase is about 2:1 to about 1:1.2.

61. A pharmaceutical formulation according to claim 19 wherein the ratio of amoxicillin free acid equivalent to organic acid equivalent in the second phase is about 1:1.

62. A formulation according to claim 1 wherein the Area Under the Curve ("AUC") (plasma concentration versus time) of the total amount of amoxicillin in the composition is substantially similar to at least 80% of the corresponding dosage of amoxycillin taken as an immediate release formulation over the same dosage period.

63. A pharmaceutical formulation according to claim 15 wherein the Area Under the Curve ("AUC") (plasma concentration versus time) of the total amount of amoxicillin in the composition is substantially similar to at least 80% of the corresponding dosage of amoxycillin taken as an immediate release formulation over the same dosage period.

64. A pharmaceutical formulation according to claim 15 wherein the Area Under the Curve ("AUC") (plasma concentration versus time) of the total amount of amoxicillin in the composition is substantially similar to at least 90% of the corresponding dosage of amoxycillin taken as an immediate release formulation over the same dosage period.

65. A pharmaceutical formulation according to claim 15 wherein the Area Under the Curve ("AUC") (plasma concentration versus time) of the total amount of amoxicillin in the composition is substantially similar to at least 100% of the corresponding dosage of amoxycillin taken as an immediate release formulation over the same dosage period.

66. A pharmaceutical formulation according to claim 15 wherein the Area Under the Curve ("AUC") (plasma concentration versus time) of the total amount of amoxicillin in the composition is bioequivalent to the corresponding dosage of amoxycillin taken as an immediate release formulation over the same dosage period.

67. A pharmaceutical formulation according to claim 15 which produces upon administration a plasma Cmax value which is two times the MIC value.

68. A method according to claim 21 wherein the bacterial infection is caused by at least one of the organisms *S. pneumoniae, H. influenzae,* and *M. catarrhalis.*

69. A method according to claim 21 wherein the duration of therapy is from about 7 to about 14 days.

70. A method of treating a respiratory tract infection in a patient in need thereof, which method comprises administering an effective amount of a formulation according to claim 1 to said patient about every 24 hours.

71. A method according to claim 70 wherein the bacterial infection is caused by at least one of the organisms *S. pneumoniae, H. influenzae,* and *M. catarrhalis.*

72. A method according to claim 70 in which the respiratory tract infection is community acquired pneumoniae, acute exacerbation of chronic bronchitis, or acute bacterial sinusitis.

73. A method according to claim 70 wherein the duration of therapy is from about 7 to about 14 days.

74. A method of treating a bacterial infection in a patient in need thereof which method comprises administering an effective amount of a formulation according to claim 15 to said patient.

75. A method according to claim 74 in which the bacterial infection is caused by at least one of the organisms *S. pneumoniae, H. influenzae,* and *M. catarrhalis.*

76. A method according to claim 74 wherein the duration of therapy is from about 7 to about 14 days.

77. A method of treating a respiratory tract infection in a patient in need thereof, which method comprises administering an effective amount of a formulation according to claim 15 to said patient about every 24 hours.

78. A method according to claim 77 in which the bacterial infection is caused by at least one of the organisms *S. pneumoniae, H. influenzae,* and *M. catarrhalis.*

79. A method according to claim 77 in which the respiratory tract infection is community acquired pneumoniae, acute exacerbation of chronic bronchitis, or acute bacterial sinusitis.

80. A method according to claim 77 wherein the duration of therapy is from about 7 to about 14 days.

\* \* \* \* \*